United States Patent [19]

Bossier, III

[11] 4,334,061

[45] Jun. 8, 1982

[54] PROCESS FOR RECOVERY OF POLYOL FATTY ACID POLYESTERS

[75] Inventor: Joseph A. Bossier, III, Greenwell Springs, La.

[73] Assignee: Ethyl Corporation, Richmond, Va.

[21] Appl. No.: 89,145

[22] Filed: Oct. 29, 1979

[51] Int. Cl.³ .......................... C07H 1/00; C07H 1/06
[52] U.S. Cl. ..................................... 536/119; 536/115; 536/20; 536/63; 536/110; 260/410.6; 560/234; 560/248
[58] Field of Search .............................. 536/119, 115; 260/410.6; 560/234, 248

[56] References Cited

U.S. PATENT DOCUMENTS 3,251,827  5/1966  Schnell et al. ...................... 536/119
3,378,543  4/1968  O'Boyle .............................. 536/119
3,384,634  5/1968  O'Boyle .............................. 536/119
3,600,186  8/1971  Mattson et al. ..................... 536/119
3,963,699  6/1976  Rizzi et al. ......................... 536/119

OTHER PUBLICATIONS

Feuge et al., "Jour. Amer. Oil Chem. Soc.", (1970), pp. 56–60.

Primary Examiner—Johnnie R. Brown
Attorney, Agent, or Firm—Donald L. Johnson; John F. Sieberth; Willard G. Montgomery

[57] ABSTRACT

A process for recovering polyol fatty acid polyesters from the crude reaction product in which it is produced by contacting with an aqueous washing medium in the presence of an emulsion decreasing organic solvent so that the alkali metal fatty acid soaps and the color-forming bodies are taken into the aqueous phase, and upon settling the phases are separated from each other.

39 Claims, No Drawings

4,334,061

PROCESS FOR RECOVERY OF POLYOL FATTY ACID POLYESTERS

BACKGROUND OF THE INVENTION

This invention relates to a high yield synthesis of polyol fatty acid polyesters, sucrose polyesters in particular, via transesterification. More specifically, this invention relates to a process having an improved purification or separation step for obtaining polyol fatty acid polyester, particularly sucrose polyesters.

The food industry has recently focused attention on polyol polyesters for use as low calorie fats in food products. See, for example, U.S. Pat. No. 3,600,186 and U.S. Pat. No. 3,963,699. As a result of this attention, there is a current need for a high yield synthesis of polyol fatty acid polyesters. Historically, such syntheses have been conducted using a mutual solvent to solubilize a polyol and esters of long-chain fatty acids, thus providing a homogenous reaction medium suitable for catalytic transesterification. One variation of this process, known as the Snell synthesis, has been employed as a means for preparing both poly- and lower-esters. However, the solvents heretofore employed in such processes are difficult to separate from the final product and are inappropriate for food uses, therefore limiting the usefulness of such synthesis in the foods industry. Accordingly, recent efforts have been directed toward the discovery of a high yield synthesis of polyol fatty acid polyesters which does not employ such solvents or provides complete separation.

Other solvent-free transesterification processes are known in the art. For example, U.S. Pat. No. 3,251,827 discloses the preparation of sucrose polyesters by means of a solvent-free interesterification using phenyl esters. However, phenol is liberated during the reaction. Phenol is also inappropriate for food use and is difficult to separate. Accordingly, this process does not satisfy current needs for a synthesis of polyol fatty acid polyesters for use in the foods industry.

Feuge, et al, "Preparation of Sucrose Esters by Interesterification", *Journal of the American Oil Chemical Society*, 47(s), 56–60 (1970), disclose a single stage solvent-free transesterification useful in synthesizing fatty acid esters of sucrose. However, this process is limited to the synthesis of lower esters. It has been experimentally determined that if the sucrose/methyl ester ratio of the Feuge et al reaction is lowered by use of excess methyl esters in an effort to synthesize polyesters, the reactants will disproportionate and precipitate sucrose which then caramelizes to form a brittle, charred waste product. Furthermore, the Feuge et al article reports low yields using lower alkyl esters. The more successful Feuge et al synthesis uses fatty acid methyl carbitol esters as starting materials. Unfortunately, methyl carbitol is, itself, inappropriate for food use. Thus, the Feuge et al process also fails to satisfy current needs for a synthesis of polyol fatty acid polyesters useful in the foods industry.

More recently, polyol fatty acid polyesters, particularly sucrose polyesters, useful in the foods industry have been prepared in high yields without solvents via transesterification by heating a mixture of a polyol, such as sucrose, a fatty acid lower-alkyl ester, an alkali metal fatty acid soap, and a basic catalyst selected from alkali metals, alkali metal alloys, alkali metal alkoxides and alkali metal hydrides at a temperature of 110°–180° and pressures of 0.1 to 760 mm Hg for a time sufficient to form a homogenous melt of partially esterified polyol and unreacted starting material, then adding excess fatty acid lower alkyl esters to the reaction product previously made to form the polyol fatty acid polyesters, and, finally, separating the polyol fatty acid polyester from the reaction mixture; see U.S. Pat. No. 3,963,699. While this process is appropriate for the foods industry and prepared polyol fatty acid polyester in a high yield with low contamination, improvements in the separation of polyol fatty acid polyester are of interest to avoid the formation of intractable emulsions, handling losses and liquid-solid separations. Further, the solvent extraction purification of the prior art does not remove color-forming impurities and it is therefore necessary to bleach the polyol fatty acid polyester with a clay. The use of a bleaching clay adds the problems of filtration and solids handling to an otherwise easily mobile liquid product with its accompanying product losses, capital expense and processing time. Accordingly, a separation, purification and recovery process for polyol fatty acid polyesters which does not have these problems would be highly desirable.

It is, therefore, an object of this invention to provide a process for the preparation of polyol fatty acid polyesters which produces such product substantially free of alkali metal fatty acid soaps and color-forming impurities.

It is a further object of this invention to provide a process for separation and recovery of polyol fatty acid polyesters in which acid/caustic refining and bleaching can be omitted.

Still a further object of this invention is the provision of an improved process for producing polyol fatty acid polyesters in which the improvement provides a separation step with simpler processing equipment, low cost reagents, high recovery of product and little, if any, emulsion formation.

These and other objects will be readily apparent from the following description of the improved process of the invention.

THE INVENTION

The present invention is based on the discovery that an aqueous washing medium in the presence of an organic solvent can be efficiently used to separate polyol fatty acid polyesters from the reaction product in which they are produced. Such combinations, as more particularly described hereinbelow, have the distinct advantages of separating the alkali metal fatty acid soaps and color-forming impurities in the aqueous phase from the polyol fatty acid polyesters remaining in the organic phase. These advantages are achieved by a liquid-liquid separation system without emulsion formation.

Specifically, the process of the invention resides in a solvent-free, low temperature process for synthesizing polyol fatty acid polyesters by transesterification of a polyol with a fatty acid ester to produce a crude reaction product containing a dark, liquid mixture of the product polyol fatty acid polyester, fatty acid alkyl esters, alkali metal fatty acid soaps and color-forming impurities, the improvement which comprises treating the crude reaction product to obtain the polyol fatty acid polyesters contained therein by the steps of contacting the crude reaction product with an aqueous washing medium while maintaining the resultant mixture at a pH of from 7 to about 12, inclusive, in the presence of an emulsion decreasing organic solvent for a period sufficient to dissolve substantial amounts of fatty acid soaps and color-forming impurities in the aqueous phase, allowing the phases to settle into an organic phase and an aqueous phase and separating the organic from the aqueous phase. In another aspect, the invention provides a solvent-free, low temperature process for synthesizing polyol fatty acid polyesters consisting essentially of:

A. heating a mixture of (i) an aliphatic or aromatic polyol having at least 2 free hydroxyl groups, (ii) a fatty acid alkyl ester, (iii) an alkali metal fatty acid soap, and (iv) a basic catalyst to a temperature and at a pressure sufficient to form a homogenous melt of partially esterified polyol and unreacted starting materials;

B. under the conditions of Step (A), adding excess fatty acid alkyl esters to the reaction product of Step (A) to form the polyol fatty acid polyester; and C. separating the polyol fatty acid polyester from the reaction product of Step (B), the improvement which comprises further characterizing said Step (C) by:

(a) contacting the reaction product of Step (B) comprising polyol fatty acid polyester, fatty acid esters, alkali metal fatty acid soaps and color-forming impurities with an aqueous washing medium in the presence of an emulsion decreasing organic solvent, said aqueous washing medium being selected from water and aqueous solutions of alkali metal compounds sufficient to maintain the mixture at a pH in the range of from 7 to 12, inclusive, and said organic solvent being selected from methanol, ethanol, isopropanol, acetone and methylethyl ketone;

(b) settling the resultant mixture for a period sufficient to form an aqueous and an organic phase;

(c) separating the aqueous phase;

(d) repeating Steps (a) through (c) on the resultant organic phase until the aqueous phase is clear; and (d) recovering the polyol fatty acid polyester substantially free of alkali metal fatty acid soaps and color-forming impurities.

One general process for preparation of polyol fatty acid poly-esters is more particularly characterized as a three-step reaction procedure with the improved process of this invention being in the third step.

Step A

In the first step of the process, a heterogenous mixture of (i) a polyol, (ii) fatty acid lower-alkyl esters, (iii) an alkali metal fatty acid soap, and (iv) a basic catalyst is reacted to form a homogenous melt comprising partially esterified polyol and unreacted starting materials.

i. As used herein, the term "polyol" is intended to include any aliphatic or aromatic compound containing at least two free hydroxyl groups. In practicing the process disclosed herein, the selection of a suitable polyol is simply a matter of choice. For example, suitable polyols may be selected from the following classes of saturated and unsaturated straight and branched chain linear aliphatics, saturated and unsaturated cyclic aliphatics including heterocyclic aliphatics, or mononuclear and polynuclear aromatics including heterocyclic aromatics. Inasmuch as the process does not employ solvents nor generate difficult-to-remove contaminants which are unappropriate to the foods industry, preferred polyols are those which have utility in the foods industry. Accordingly, the carbohydrates and food grade glycols are preferred polyols. Carbohydrates are polyhydroxy aldehydes or polyhydroxy ketones, or substances that yield such compounds on hydrolysis. They are distributed universally in plants and animals and make up one of the three important classes of animal foods. Carbohydrates may be subdivided into three important classes; the monosaccharides, oligosaccharides, and the polysaccharides. Monosaccharides include those carbohydrates which do not hydrolyze. Accordingly, monosaccharides suitable for use herein include, for example, glucose, mannose, galactose, arabinose, xylose, ribose, apiose, rhamnose, psicose, fructose, sorbose, tagitose, ribulose, xylulose, and erythrulose. Oligosaccharides are carbohydrates which yield only a few molecules of monosaccharides on hydrolysis. Accordingly, oligosaccharides suitable for use herein include, for example, maltose, kojibiose, nigerose, cellobiose, lactose, melibiose, gentiobiose, turanose, rutinose, trehalose, sucrose, and raffinose. Polysaccharides are those carbohydrates which yield a large number of molecules of monosaccharides on hydrolysis. Accordingly, polysaccharides suitable for use herein include, for example, amylose, glycogen, cellulose, chitin, inulin, agarose, zylans, mannan, and galactans. Another class of polyols preferred herein is the sugar alcohols. Although sugar alcohols are not carbohydrates in a strict sense, the naturally occurring sugar alcohols are so closely related to the carbohydrates that they are also preferred for use herein. The sugar alcohols most widely distributed in nature and suitable for use herein are sorbitol, mannitol, and galactitol. Preferred carbohydrates and sugar alcohols suitable for use herein include, for example, xylitol, sorbitol and sucrose.

ii. As used herein, the term "fatty acid lower alkyl esters" is intended to include the $C_1$ and $C_2$ esters of fatty acids containing about 8 or more carbon atoms, and mixtures of such esters. Suitable esters can be prepared by the reaction of diazoalkanes and fatty acids, or derived by alcoholysis from the fatty acids naturally occurring in fats and oils. If the acids are derived from fats, saturated acids predominate, but if derived from oils, unsaturated acids predominate. Accordingly, suitable fatty acid lower-alkyl esters can be derived from either saturated or unsaturated fatty acids. Suitable preferred saturated fatty acids include, for example, capric, lauric, palmitic, stearic, behenic, isomyristic, isomargaric, myristic, caprylic and anteisoarachadic. Suitable preferred unsaturated fatty acids include, for example, maleic, linoleic, licanic, oleic, linolenic and erythrogenic acids. Mixtures of fatty acids derived from soybean oil, sunflower oil, safflower oil and corn oil are especially preferred for use herein.

Unusually high yields, i.e., greater than 90% of polyol fatty acid polyesters have been obtained where methyl esters are used in accordance with the process herein. Accordingly, methyl esters are the preferred fatty acid lower-alkyl esters.

iii. As used herein, the term "alkali metal fatty acid soap" is intended to include the alkali metal salts of saturated and unsaturated fatty acids having from about 8 to about 18 carbon atoms. Accordingly, suitable alkali metal fatty acids soaps include, for example, the lithium, sodium, potassium, rubidium, and cesium salts of fatty acids such as capric, lauric, myristic, palmitic, licanic, parinaric and stearic acids. Mixtures of fatty acids derived from soybean oil, sunflower oil, safflower oil and corn oil are preferred for use herein. Accordingly, preferred alkali metal fatty acid soaps include, for example, the potassium soap made from safflower oil fatty acids, the potassium soap made from soybean oil fatty acids, and the sodium soap made from sunflower oil fatty acids.

iv. The basic catalysts suitable for use herein are those selected from the group consisting of alkali metals such as sodium, lithium and potassium; alloys of two or more alkali metals such as sodium-lithium and sodium-potassium alloys; alkali metal hydrides such as sodium, lithium and potassium hydride; and alkali metal alkoxides such as potassium t-butoxide and sodium methoxide.

In a preferred embodiment of this polyol fatty acid polyester preparation, the catalyst is dispersed in a suitable carrier so as to insure uniform distribution of the catalyst throughout the reaction mass. Suitable carriers or dispersing agents include, for example, hydrocarbon solvents, such as xylene; and polyol octaesters, such as sucrose octaesters. Octaesters derived from the polyol being esterified are preferred carriers since their use avoids contamination or removal problems. Preferred catalysts suitable for use herein include, for example, sodium hydride, potassium hydride, a dispersion of potassium in sucrose octaester, potassium t-butoxide, and sodium methoxide.

In carrying out Step A, the above-described reactants are combined to form a heterogenous mixture. The precise ratio of reactants can be freely selected from within the guidelines set forth hereinafter. However, routine experimentation may be necessary in order to establish the optimum concentrations for a given set of reactants. In general, the heterogenous mixture comprises from about 10% to about 50%, preferably from about 20% to about 30% by weight of a polyol; from about 40% to about 80%, preferably from about 50% to about 70% by weight of fatty acid lower-alkyl esters; from about 1% to about 30%, preferably from about 5% to about 10% by weight of an alkali metal fatty acid soap; and from about 0.05% to about 5%, preferably from about 0.1% to about 0.5% by weight of a basic catalyst selected from the group consisting of alkali metals, alloys of two or more alkali metals, alkali metal alkoxides and alkali metal hydrides. The heterogenous mixture is heated to a temperature within the range of from about 110° C. to about 180° C., preferably from about 130° C. to about 145° C. under a pressure of from about 0.1 mm Hg to about 760 mm Hg, preferably from about 0.5 mm Hg to about 25 mm Hg. Within these temperature and pressure ranges, a homogenous melt of partially esterified polyol and unreacted starting materials will form in from about 2 to 4 hours.

It may be desirable to initiate the reaction by initially introducing from about 0.1% to about 1%, by weight, of catalyst and, thereafter, introducing additional catalyst as the reaction proceeds.

Step B

In the second step of the process for producing polyol fatty acid polyesters for separation by the process of the instant invention, excess fatty acid lower-alkyl esters are added to the homogenous melt formed in Step A. As used herein, the term "excess" is intended to include sufficient lower-alkyl esters to raise the overall ester:polyol mole ratio above 10:1, preferably to about 16:1. Although ratios beyond 16:1 can be used, as a general rule, such ratios do not noticeably decrease reaction time or improve the yield and are therefore impractical.

It should be noted that as the transesterification proceeds, a lower alcohol is formed as a by-product. In order to promote the reaction, the alcohol by-product is preferably removed. Many removal techniques are known in the art, any one of which can be used to effectively and efficiently remove the lower alcohol. Vacuum removal both with and without an inert gas sparging has been found to promote the reaction. However, for practical purposes, simple distillation under atmospheric pressure has been found to be sufficient. In any event, the formation of a lower alcohol presents no significant obstacle to the use of the polyol fatty acid polyester by the foods industry.

Step C

In the third step of the process, the polyol fatty acid polyesters formed in Step B are separated from the alkali metal fatty acid soap and color-forming impurities contained in the crude reaction product. The reaction product is a dark, liquid mixture containing the polyol fatty acid polyesters, excess fatty acid lower alkyl esters, alkali metal fatty acid soaps, a trace of lower alcohol, unreacted starting materials and some thermal degradation products, including color-forming impurities and caramelized sugar. Separation of the polyol fatty acid polyesters can be accomplished by contacting the reaction product of Step (B) with an aqueous washing medium in the presence of an emulsion decreasing organic solvent. The aqueous component has the function of dissolving, inter alia, the alkali metal fatty acid soaps and color-forming impurities. As such, it should maintain the alkali metal fatty acid soaps on the basic side of the acid-base pH scale. This prevents formation of the free acids. Accordingly, the aqueous washing medium can be water or an aqueous solution of alkali metal compounds selected from alkali metal carbonates, bicarbonates and hydroxides. Typical of such basic alkali metal compounds are sodium carbonate, sodium bicarbonate, sodium hydroxide, potassium hydroxide, potassium carbonate, potassium bicarbonate and the like. The aqueous washing medium used should be sufficient to maintain the reaction product of Step (B) in a condition so that acidification of the alkali metal fatty acid soap does not occur. However, the reaction product of Step (B) should not be so basic that saponification of the excess fatty acid lower alkyl esters occurs yielding more "soaps". For example, the aqueous washing medium should be sufficient to maintain the reaction product of Step (B) at a pH of from 7 to about 12 so that saponification is prevented. Preferably, the aqueous washing medium is selected from water, aqueous sodium carbonate and aqueous sodium hydroxide. When aqueous sodium hydroxide is employed, the concentration can be relatively low. That is, a dilute caustic solution can be advantageously employed in the process of this invention. By the term "dilute caustic" is meant a solution of 0.1 to 2.5% by weight of sodium hydroxide in water. More preferably, the sodium hydroxide concentration is from about 0.25 to about 0.5% by weight. At such concentrations the undesired saponification of excess fatty acid lower-alkyl esters does not take place and, also, emulsions are avoided.

The contacting of the reaction product of Step (B) with the aqueous washing medium is carried out in the presence of an organic solvent. The contacting of Step (C) is thus facilitated by a material which readily decreases formation of emulsion in the resultant mixture in Step (C). The decrease in formation of emulsions is very important to prevent physical loss by entrainment of product polyol fatty acid polyesters in the emulsion which is a waste material. The organic solvent is preferably a protonic or aprotic solvent. More preferably, the organic component is a solvent which is partially solubilized in both the aqueous and organic phases and aids in the formation of a true solution rather than a slurry upon contacting the reaction product of Step (B) with the aqueous washing medium. It has been found that solvents which posses such advantageous properties and are preferred embodiments of the organic solvent are selected from methanol, ethanol, isopropanol, acetone, methyl ethyl ketone and the like. The organic solvent most preferable for its advantageous properties, availability, and suitability for use in edible products is isopropanol.

In contacting the reaction product of Step (B) with the aqueous washing medium, a unique relationship has been discovered between the washing medium and the reaction product of Step (B), as well as between the washing medium and the organic solvent. It has been found that a sufficient amount of the washing medium must be used; otherwise, color-forming impurities are not removed. In contrast, using too great an amount of washing medium carries the penalties of large volume, expensive chemical process equipment and high processing costs. It has been determined that from 10 to about 100% by weight, based on the reaction product of Step (B) of the aqueous washing medium can be used to satisfactorily avoid emulsion formation, remove the color-forming impurities from the reaction product of Step (B), and strike a balance between uneconomically higher cost equipment and processing costs on one hand and effective reactant usage on the other hand.

Of course, if economics are not considered, it is possible to contact the reaction product of Step (B) with amounts of aqueous washing medium well below 10 weight percent and do so great numbers of times. Likewise, it is also possible to use amounts of aqueous washing medium greater than 100 weight percent. Further, the lower the amount of aqueous washing medium the greater the number of washings and, conversely, the greater the amount of washing medium the fewer the number of washings are employed. However, it appears that about 100 weight percent of aqueous washing medium, based on the reaction product of Step (B), is a reasonable upper limit in view of the size of the reaction vessel, the processing costs and auxiliary equipment required. More preferably, the washing medium is employed in the range of 20 to about 50 percent by weight based on the reaction product of Step (B).

The relationship of the aqueous washing medium component to the organic solvent is also of concern in order to prevent the formation of emulsions. It has been determined that a weight ratio greater than 1:1 of the aqueous washing medium to the organic solvent is advantageous to prevent the formation of emulsions during the contacting. Preferably from 1:1 to 25:1 weight ratios of the aqueous washing medium to the organic solvent are employed. In general, it is practical to conduct the washing in several stages with increasing ratios of aqueous washing medium to organic solvent. For example, a first wash is carried out at a weight ratio of from 3:1 to about 7:1 of aqueous washing medium to organic solvent. After an initial contacting step has been carried out, if it is desired to carry out a second washing, the ratio of aqueous washing medium to organic solvent can be increased to from 5:1 to about 15:1; for a third contacting step the weight ratio of aqueous washing medium to organic solvent can range from 15:1 to about 25:1. The reason that the greater amounts of aqueous component can be employed is that the first contacting or washing removes the major amount of the alkali metal fatty acid soaps. Hence, the succeeding washings do not have the tendency toward emulsion and the organic solvent can be reduced. In a most highly preferred process of the invention, the contacting of Step (C) is carried out by three successive washings with the ratio of aqueous washing medium to organic solvent being at least 5:1 by weight in the first washing; at least 10:1 in the second washing; and at least 20:1 in the third washing.

Of course, every washing procedure requires sufficient agitation to insure contact between the components of the mixture but without the vigorous agitation which would favor the formation of emulsions. Then, between each successive contacting, the agitation is stopped, the phases are allowed to settle and the aqueous layer is discarded or sent to reactant recovery or waste treatment. The successive washing or contacting procedure is followed until the aqueous discard layer appears clear and is substantially free of alkali metal fatty acid metal soap and color-forming impurities. The contacting time can be from 15 minutes to about 1 hour, depending upon the size of reaction vessels and agitation, but it is only necessary to insure efficient contacting of the reaction product of Step (B) with the aqueous washing medium. The contacting temperature can range from about 25° to about 100° C. and is preferably about 75° C. to insure fluidity of the reaction mixture and increase solubilities. After contacting and stopping agitation, the reaction mixture forms two phases, an organic phase and an aqueous phase. Sufficient settling time is required to insure efficient separation of the phases. For example, separation times of 15 minutes to several hours can be employed. At contacting temperatures of 75° C., it is preferred to allow phase separation or settling to occur in from 30 minutes to 1 hour.

The aqueous phase can then be discarded and the polyol fatty acid polyesters can be treated by conventional procedures to remove traces of water, solvent and alcohols, such as methanol, by acidifying, for example, adding 0.5 weight percent of glacial acetic acid based on the resultant polyol fatty acid polyester, vaccum stripping and solvent extraction. The polyol fatty acid polyester is then ready for recovery from the organic phase by solvent extraction to remove excess fatty acid lower alkyl esters and steam stripping to remove trace amounts of residual fatty acid lower alkyl esters and solvent.

In general, the procedure which is employed in the improved process of this invention includes the following steps:

Heat a mixture of alkali metal fatty acid soap, fatty acid lower alkyl esters, and polyol to 150° C. at not more than 10 mm Hg. Then, add 0.1 weight percent, based on the weight of the mixture, of alkali metal hydride catalyst, maintaining with moderate agitation at temperature for about 1.5 hours, and adding a second charge of catalyst and maintaining for another 1.5 hours to form a homogenous melt. Then, add an additional charge of fatty acid lower alkyl esters to make 16 times the amount of polyol and 0.25 weight percent of potassium hydride catalyst, based on the mixture, and heat for 2 hours at temperature, and, finally, add 0.15 weight percent of potassium hydride catalyst and cook for a final 2-hour period. A sample analyzed by thin layer chromatography is used to tell whether the product is ready for the separation procedure.

If the analysis shows little unreacted starting material, the reaction product is cooled to 75° C. and 30 weight percent, based on the reaction product, of washing medium made up of 5 parts of 0.25-0.5 weight percent aqueous sodium hydroxide to one part of isopropanol is added to the reaction product and agitated for 15 to 30 minutes at 75° C. The agitation is stopped and the phases allowed to settle for 15 to 30 minutes. Then the dark, soapy aqueous phase is discarded. The washing procedure is repeated with an increased ratio of dilute caustic to isopropanol of 10:1 and then the washing procedure is repeated a third time at a 20:1 ratio of dilute caustic to isopropanol. This procedure is repeated a fourth time if the aqueous layer is not sufficiently clear and color-free by visual inspection. The phases are settled and the clear aqueous layer is discarded. Then to the refined polyol fatty acid polyester is added 0.5 weight percent of glacial acetic acid based on the weight of the organic phase. The acidified reaction mixture is agitated for 10 to 15 minutes at 75° C. The residual isopropanol, water and acetic acid is then steam stripped under vacuum at 75°-100° C. Then, the excess fatty acid methyl esters are extracted with methanol using countercurrent flow in a packed column and finally the polyol is deodorized by sparging steam at 100° C. and 100 mm Hg and then nitrogen at 135° C. until cooled to 40° C. The polyol fatty acid polyesters are then packaged under nitrogen.

The improved process of the present invention will be more readily appreciated from consideration of the following examples. The examples are non-limiting and illustrative only.

EXAMPLES 1-5

These examples illustrate the improved process of the present invention. Using a similar procedure, as described below, in each example for producing the crude reaction product, it was then treated according to the improved separation step as described hereinabove with varying aqueous washing media. The results in product quality and overall yield after using the improved process are compared with a process employing known separation procedure, e.g., Example 1 of U.S. Pat. No. 3,963,699, as shown in Table 1.

Example 1: To a suitable reactor was charged 136.5 g of fatty acid methyl esters, derived from safflower oil esterification with methanol and 16 g of potassium hydroxide in methanol. The mixture is heated to 110° C. at atmospheric pressure over a period of 40 minutes. Then, vacuum is applied while the temperature is held for 30 minutes. Afte being left cool overnight, the mixture is heated to 110° C. and 42 g of sugar is charged to the reactor. Full vacuum is applied and the temperature is increased to 150° C., within 30 minutes. Then, 1/6 of the total weight of potassium hydride catalyst (calculated as three times from 0.15-0.2 weight percent of the total weight of fatty acid methyl esters plus sugar added, or 0.8-1.070 g of total catalyst) or about 0.133-0.178, is charged to the reactor while heating at temperature for 1½ hours. Thereafter, another 1/6 of potassium hydride catalyst is added while maintaining temperature for 1½ hours. Then, 545.5 g of fatty acid methyl esters derived from safflower oil methanolysis are charged and the reaction mixture is filtered to remove unreacted sugar. About 0.3 g of sugar is recovered.

The filtered reaction mixture is then heated to 150° C. in a suitable reactor in 1 hour and a charge of catalyst somewhat greater than ⅓ of the total is added with the temperature being maintained for 2 hours thereafter. The remaining catalyst is then added and the reaction mixture is held at temperature for 2 hours. The heat and vacuum are then shut off and the reaction mixture is cooled to 100° C. in 30 minutes. The agitator is turned off and a nitrogen purge is put on the system.

The crude reaction product, 563 g, is placed in a reactor and heated to 75° C. Then, there is charged 30 weight percent, based on the crude reaction product, of a mixture of 5 parts 0.25 weight percent NaOH to 1 part isopropanol at room temperature. The reaction mixture is agitated until the temperature is again 75° C., then agitation is stopped and the layers are settled for 15 minutes before the aqueous phase is removed. This procedure is repeated 3 times, except that the last wash is just with water. The water is then flashed from the organic phase and the organic phase is extracted with methanol in a countercurrent packed column and given 3 hand shaken methanol washes at 50°-60° C. The organic phase is then filtered through a course glass frit. During the filtration, the sample was dropped. Thus, a material balance could not be obtained. The analysis of the final product sucrose polyester is given in Table 1.

EXAMPLE 2

The procedure of Example 1 is followed except that the reaction mixture is not filtered to remove unreacted sugar. Further, the process was interrupted between production of the crude sucrose polyester and refining, being left under nitrogen for the week-end.

The crude product, 558.2 g, was charged to a suitable reactor, heated to 75° C. and a room temperature mixture of 139.55 g of water and 27.91 g of isopropanol was added. The reaction mixture was heated back to 75° C. with agitation after 10 minutes, settled for 20 minutes and the aqueous phase removed. This procedure was repeated a second time, except that the wash took 10 minutes, a third wash in the same manner was made. Finally, a fourth wash in the same manner except that 2.8 g of glacial acetic acid was included. Some rag layer was noted in this washing procedure.

The washed organic phase was transferred to a continuous extraction column and the safflower oil methyl esters were extracted with methanol at 60° C. over a period of 24 hours. The residual methanol was removed from the extracted organic by heating to 100° C. under vacuum and sparging with nitrogen. The weight of the final sucrose polyester product was 254.5 g. The results and analysis of this example are given in Table 1.

EXAMPLE 3

A third sample of sucrose polyester was produced following the procedure of Example 1, except that only 500 g of excess safflower oil methyl esters were added and an additional 0.13 g of potassium hydride catalyst was added over and above the normal amount.

The crude reaction product containing the sucrose polyester was refined using three successive washes containing 5 parts of 0.5 weight percent $Na_2CO_3$ and 1 part isopropanol at about 30% by weight of washing medium based on the crude reaction product. The procedure was the same each time with 15 minutes agitation and 15 minutes settling followed by removal of the aqueous phase. A fourth wash with 5 parts of water to 1 part of isopropanol and 0.005 weight percent glacial acetic acid based on the crude sucrose polyester was used to wash the product. The washed product was heated to 60°-75° C. and stripped with nitrogen under vacuum for 30 minutes to remove traces of water, isopropanol and acetic acid. It was then filtered and extracted continuously with methanol for 36 hours, followed by 4 hand shaken methanol washes at 60° C. Residual methanol was stripped using nitrogen at 100° C. The final product weight was 265° C. The analysis and results are given in Table 1.

EXAMPLE 4

Following the procedure of Example 1, another sample of crude sucrose polyester was prepared. The crude product was given four washes at 75° C. with a mixture of 5 parts 0.5 weight percent caustic to 1 part of isopropanol using 30 weight percent of the aqueous washing medium based on the weight of crude sucrose polyester. The wash procedure was to agitate for 15 minutes, settle for 15 minutes and then separate the aqueous phase. After the fourth wash, 0.5 weight percent of glacial acetic acid based on the crude sucrose polyester reaction product was added. The mixture was heated to 75° C. for 5 minutes. Then, the residual isopropanol, water and acetic acid was vacuum stripped with nitrogen at 60°-75° C. The washed product was filtered and continuously extracted with methanol for about 60 hours. In addition, four hand shaken extractions with methanol were carried out at 50°-60° C. at a 5:1 weight ratio of methanol to product. The extracted product was stripped with nitrogen at 100° C. and 300 mm Hg for 30 minutes. The final product was filtered and 274 g were obtained. The analysis and results of this example are given in Table 1.

EXAMPLE 5

Following the procedure of Example 1, except that 514 g of excess methyl esters were added, a crude sucrose polyester was produced. The crude product was washed four times with a washing medium containing in the first wash 5 parts of 1 weight percent caustic to 1 part of isopropanol, in the second wash 11 parts of 1 weight percent caustic to 1 part of isopropanol, in the third and fourth washes 21.5 parts of 1 weight percent caustic to 1 part of isopropanol. All washes used 30 weight percent washing medium based on the crude sucrose polyester. The procedure was to agitate for 15 minutes, settle for 15 minutes and then separate the aqueous phase. After the fourth wash, 0.5 weight percent of glacial acetic acid, based on the crude product, was added at 75° C. Then, after about 5 minutes, the residual isopropanol, water and acetic acid were stripped off with nitrogen under vacuum at 60°-75° C. An additional 3 g of glacial acetic acid was added and without filtration the product was then continuously extracted with methanol for about 36 hours. An additional seven hand shaken extractions with methanol were carried out. Then, the product was stripped with nitrogen at 100° C. and 200 mm Hg. The final product weight was 267.5 g and the results and analyses are given in Table 1.

In the above examples, all parts given are parts by weight.

TABLE 1

| Examples | 1 | 2 | 3 | 4 | 5 | Comparative |
| --- | --- | --- | --- | --- | --- | --- |
| Aqueous Washing Media* | Caustic/IPA | $H_2O$/IPA | $Na_2CO_3$/IPA | Caustic/IPA | Caustic/IPA | — |
| Safflower Oil Utilization (S.O./lb SPE) | N.A.** | 1.4 | 1.20 | 1.25 | 1.30 | 2.55 |
| Residual Isopropanol, ppm | <15 | <15 | <15 | <15 | <15 | — |
| Hydroxyl Value | 5.6 | 9.1 | 8.3 | 4.2 | 4.3 | 11, 9 |
| Residual Methyl Esters, ppm | ~50 | ~50 | ~175 | ~100 | ~50 | 75, 100 |
| Residual MeOH, ppm | <15 | <15 | <15 | <15 | <15 | 1, 1 |
| Free Fatty Acids, % weight | <.05 | <.05 | <.05 | <.05 | <.05 | 0.1, .05 |
| Relative Ester Composition, % weight | | | | | | |
| Octa | 72.8 | 66.4 | 67.4 | 73.4 | 82.1 | 65 |
| Hepta | 24.8 | 30.4 | 30.0 | 24.5 | 16.1 | 29 |
| Hexa | 2.4 | 3.2 | 2.6 | 2.1 | 1.8 | 6 |
| Yield (% of theory)≠ | N.A.** | 91 | 95 | 95+ | 95+ | 66.5 |

*Aqueous washing media:
- Caustic is 0.25–1.0 weight percent aqueous NaOH
- $Na_2CO_3$ is 0.5 weight percent aqueous $Na_2CO_3$
- Ratio of aqueous to organic, by weight is 5:1 for all washes in Examples 1–4 and in Example 5 1st wash, 5:1; 2nd wash, 10:1; 3rd and 4th wash, 20:1
**Not available - accidentally spilled final product
≠Basis of yield is percent of recovery of 100% conversion of sucrose to 7.5 polyester product.

From the above results, it is at first clear that the improved process produces a product of quality similar to or better than the prior art process. However, unexpectedly, the yield based on theoretically expected results is improved by over 40%. This is because the handling and saponification losses are drastically reduced in the liquid-liquid separation system as opposed to the prior art liquid-solid separation process using acid and caustic refining technique followed by clay bleaching agents.

Having described the improved process of this invention, one skilled in the art will be able to envision changes in the process within the scope and spirit of this invention. Therefore, it is desired that the invention be limited only by the lawful scope of the following claims.

What is claimed is:

1. In a solvent-free, low temperature process for synthesizing polyol fatty acid polyesters by transesterification of a polyol with a fatty acid ester to produce a crude reaction product containing a dark, liquid mixture of the product polyol fatty acid polyester, fatty acid alkyl esters, alkali metal fatty acid soaps and color-forming impurities, the improvement which comprises treating the crude reaction product to obtain the polyol fatty acid polyesters contained therein by the steps of contacting the crude reaction product with an aqueous washing medium while maintaining the resultant mixture at a pH of from 7 to about 12, inclusive, in the presence of an emulsion decreasing organic solvent at a temperature of from about 25° C. to about 100° C. for a period of time of from about 15 minutes to at least three hours to dissolve substantial amounts of fatty acid soaps and color-forming impurities in the aqueous phase, allowing the phases to settle into an organic phase and an aqueous phase and separating the organic from the aqueous phase.

2. The process of claim 1 in which said solvent is a polar solvent.

3. The process of claim 1 in which said solvent is selected from acetone, methyl ethyl ketone, methanol, ethanol and isopropanol.

4. The process of claim 1 in which said polyol fatty acid polyester is selected from sorbitol, xylitol and sucrose.

5. The process of claim 1 in which said polyol fatty acid polyester is sucrose.

6. The process of claim 1 in which said aqueous washing medium is selected from water and aqueous solutions of alkali metal compounds.

7. The process of claim 1 in which said washing medium is water.

8. The process of claim 1 in which said washing medium is an aqueous solution of an alkali metal compound.

9. The process of claim 8 in which said aqueous alkali metal compound is selected from aqueous solutions of sodium hydroxide, potassium hydroxide, sodium carbonate, potassium carbonate, sodium bicarbonate and potassium bicarbonate.

10. The process of claim 8 in which said aqueous alkali metal compound is a dilute solution of the alkali metal compound.

11. The process of claim 1 in which said polyol is treated with from 10 to about 100 percent by weight based on the crude reaction product containing said polyol of said aqueous washing medium.

12. The process of claim 1 in which said polyol is treated with from about 20 to about 40 percent by weight based on the crude reaction product containing said polyol of said aqueous washing medium.

13. The process of claim 1 in which the weight ratio of said aqueous washing medium to said organic solvent ranges from 1:1 to about 10:1.

14. The process of claim 1 in which the weight ratio of said aqueous washing medium to said organic solvent ranges from about 3:1 to about 7:1.

15. The process of claim 1 in which the steps of contacting, allowing phases to settle and separating the phases is carried out for at least three successive times.

16. The process of claim 15 in which the three successive washings are conducted using from 20 to about 40 percent of an aqueous washing medium selected from dilute aqueous alkali metal compounds and having a weight ratio of an aqueous washing medium to organic solvent of from 3:1 to 7:1 in the first wash, from 5:1 to 15:1 in the second wash and from 15:1 to not greater than 25:1 in the third and subsequent wash.

17. The process of claim 1 in which said organic solvent is isopropanol.

18. The process of claim 1 in which said aqueous washing medium is dilute aqueous caustic.

19. The process of claim 1 in which said organic solvent is isopropanol and said aqueous washing medium is dilute aqueous caustic.

20. In a solvent-free, low temperature process for synthesizing polyol fatty acid polyesters consisting essentially of:

A. heating a mixture of (i) an aliphatic or aromatic polyol having at least 2 free hydroxyl groups, (ii) a fatty acid alkyl ester, (iii) an alkali metal fatty acid soap, and (iv) a basic catalyst to a temperature and at a pressure sufficient to form a homogeneous melt of partially esterified polyol and unreacted starting materials;

B. under the conditions of Step (A), adding excess fatty acid alkyl esters to the reaction product of Step (A) to form the polyol fatty acid polyester; and C. separating the polyol fatty acid polyester from the reaction product of Step (B), the improvement which comprises:

(a) contacting the reaction product of Step (B) comprising polyol fatty acid polyester, fatty acid esters, alkali metal fatty acid soaps and color-forming impurities with an aqueous washing medium in the presence of an emulsion decreasing organic solvent, said aqueous washing medium being selected from water and aqueous solutions of alkali metal compounds sufficient to maintain the mixture at a pH in the range of from 7 to 12, inclusive, and said organic solvent being selected from methanol, ethanol, isopropanol, acetone and methylethyl ketone;

(b) settling the resultant mixture for a period sufficient to form an aqueous and an organic phase;

(c) separating the aqueous phase;

(d) repeating Steps (a) through (c) on the resultant organic phase until the aqueous phase is clear; and (e) recovering the polyol fatty acid polyester substantially free of alkali metal fatty acid soaps and color-forming impurities.

21. The improved process of claim 20 in which said aqueous washing medium is water.

22. The improved process of claim 20 in which said aqueous washing medium is selected from aqueous mixtures of sodium carbonate, sodium bicarbonate, potassium hydroxide and sodium hydroxide.

23. The improved process of claim 20 in which said aqueous washing medium is aqueous sodium hydroxide.

24. The improved process of claim 1 in which said aqueous washing medium is dilute aqueous sodium hydroxide.

25. The improved process of claim 20 in which said washing medium is from 10 to about 100% by weight based on the reaction product of said Step (B) and where the weight ratio of the aqueous washing medium to the organic solvent in said Step (a) ranges from 3:1 to 7:1 by weight.

26. The improved process of claim 20 in which said aqueous washing medium is from 20 to about 50% by weight based on the reaction product of said Step (B).

27. The improved process of claim 20 in which the organic solvent is isopropanol.

28. The improved process of claim 20 in which Steps (a) through (c) are carried out three times in succession.

29. The improved process of claim 28 in which the contacting or washing of the reaction product of said Step (B) is carried out three successive times the first wash having at least a weight ratio of the aqueous washing medium to the organic solvent, ranging from 3:1 to 7:1, the second wash having a weight ratio of the aqueous washing medium to the organic solvent of 5:1 to 15:1, and the third wash having a weight ratio of the aqueous washing medium to the organic solvent ranging from 15:1 to not greater than 25:1.

30. The improved process of claim 20 in which said aqueous component is dilute aqueous sodium hydroxide and said organic component is isopropanol.

31. The improved process of claim 20 in which there is employed from 20 to about 50 percent by weight based on the reaction product of said Step (B) of an aqueous washing medium which is dilute caustic, the organic solvent is isopropanol and the contacting or washing of the reaction product of said Step (B) is carried out three sucessive times the first wash having at least a weight ratio of the aqueous washing medium to the organic solvent, ranging from 3:1 to 7:1, the second wash having a weight ratio of the aqueous washing medium to the organic solvent of 5:1 to 15:1, and the third wash having a weight ratio of the aqueous washing medium to the organic solvent ranging from 15:1 to not greater than 25:1.

32. The improved process of claim 20 in which the polyol is a disaccharide.

33. The improved process of claim 20 in which said polyol is selected from the group consisting of sucrose, xylitol and sorbitol.

34. The improved process of claim 33 in which the aqueous washing medium is dilute caustic, the organic solvent is isopropanol and the reaction product of said Step (B) is contacted with from 20 to about 50% by weight of the aqueous washing medium based on the reaction product of said Step (B).

35. The improved process of claim 20 in which the fatty acid alkyl esters are fatty acid methyl esters.

36. The improved process of claim 20 in which the methyl esters are derived from natural oils selected from the group consisting of soybean oil, sunflower oil, safflower oil and corn oil.

37. The improved process of claim 36 in which the reaction product of said Step (B) is contacted with from 20 to about 50% by weight of an aqueous washing medium based on the reaction product of said Step (B), which is dilute aqueous sodium hydroxide and said organic solvent being isopropanol.

38. The improved process of claim 20 in which the polyol is sucrose.

39. The improved process of claim 38 in which the reaction product of said Step (B) is contacted with from 20 to about 50% by weight of an aqueous washing medium based on the reaction product of said Step (B), which is dilute aqueous sodium hydroxide said organic solvent being isopropanol, and the contacting or washing of the reaction product of said Step (B) being carried out at least three successive times the first wash having at least a weight ratio of the aqueous washing medium to the organic solvent, ranging from 3:1 to 7:1, the second wash having a weight ratio of the aqueous washing medium to the organic solvent of 5:1 to 15:1, and the third wash having a weight ratio of the aqueous washing medium to the organic solvent ranging from 15:1 to not greater than 25:1.

* * * * *

UNITED STATES PATENT AND TRADEMARK OFFICE
CERTIFICATE OF CORRECTION

PATENT NO. : 4,334,061

DATED : June 8, 1982

INVENTOR(S) : Joseph A. Bossier III

It is certified that error appears in the above-identified patent and that said Letters Patent is hereby corrected as shown below:

Column 1, line 67, reads "110°-180°", should read --110°-180°C--.

Column 2, line 8, reads "prepared", should read --prepares--.

Column 9, line 57, reads "afte", should read --after--.

Signed and Sealed this

Thirty-first Day of May 1983

[SEAL]

Attest:

DONALD J. QUIGG

Attesting Officer     Acting Commissioner of Patents and Trademarks